United States Patent [19]

Hara et al.

[11] 4,242,429
[45] Dec. 30, 1980

[54] METHOD OF STABILIZING ORGANIC SUBSTRATE MATERIALS AGAINST LIGHT

[75] Inventors: Hiroshi Hara, Asaka; Yoshiaki Suzuki, Minami-ashigara, both of Japan

[73] Assignee: Fuji Photo Film Co., Ltd., Minami-ashigara, Japan

[21] Appl. No.: 955,840

[22] Filed: Oct. 30, 1978

[30] Foreign Application Priority Data

Nov. 1, 1977 [JP] Japan .............................. 52-132274

[51] Int. Cl.³ ............................................. G03C 7/00
[52] U.S. Cl. ..................................... 430/17; 430/216;
430/372; 430/382; 430/384; 430/386; 430/388;
430/544; 430/551; 430/933; 260/429 R;
260/439 R
[58] Field of Search .................. 96/56, 67, 74, 84 R,
96/84 UV, 66.4, 109, 110, 114.5, 119, 77, 100;
252/300 R; 260/429 R, 429 L, 429 J, 438.1, 439 R

[56] References Cited

U.S. PATENT DOCUMENTS

| | | | |
|---|---|---|---|
| 3,161,520 | 12/1964 | Rauch et al. | 96/84 R |
| 3,588,216 | 6/1971 | Bloom | 260/429 R |
| 3,672,898 | 6/1972 | Schwan et al. | 96/74 |
| 4,050,938 | 9/1977 | Smith, Jr. et al. | 96/84 UV |

FOREIGN PATENT DOCUMENTS 1451000 9/1976 United Kingdom ...................... 96/109

OTHER PUBLICATIONS

Bayer, Angew. Chem., vol. 73, 1961, p. 659, GDCH-Ortsverband Bonn.

Jadamus et al., J.A.C.S., 86, 1964, p. 3056, Metal Ion Induced Rearrangements.
Cicchetti, Adv. Polymere Sci., vol. 7, pp. 70-112 (1970), Mech. of Oxid. Photodegradation and UV Stabilization of Polyolefins.

*Primary Examiner*—Travis Brown
*Attorney, Agent, or Firm*—Sughrue, Rothwell, Mion, Zinn and Macpeak

[57] ABSTRACT

The stability of organic substrate materials having an absorption peak between 300 and 800 nm in wavelength can be improved by the presence of a compound having the following general structural formula (I):

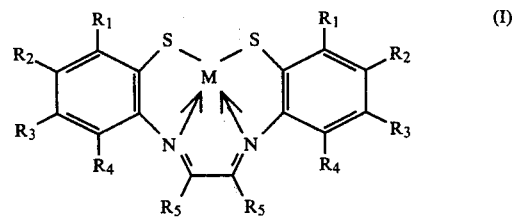

wherein M represents Cu, Co, Ni, Pd or Pt; $R_1$, $R_2$, $R_3$ and $R_4$ each represents a hydrogen or halogen atom, a cyano, an alkyl, an aryl, a cycloalkyl, or a heterocyclic group which may be substituted or unsubstituted and which is attached to the carbon atom in the benzene ring directly or through a divalent connecting group; alternatively, each of $R_1$ and $R_2$, $R_2$ and $R_3$, or $R_3$ and $R_4$ may combine to form the non-metallic atoms necessary to complete a 6-membered ring; and $R_5$ represents a hydrogen atom or methyl.

12 Claims, No Drawings

METHOD OF STABILIZING ORGANIC SUBSTRATE MATERIALS AGAINST LIGHT

BACKGROUND OF THE INVENTION

1. Field of the Invention

This invention relates to improving the light fastness of organic substrate materials and, more particularly, to improving the light fastness of organic compounds useful as dyestuffs. The present invention is particularly directed to improving the light fastness of organic substrate materials occurring in photographic materials, e.g., color films, prints, etc.; in colored polymers useful as agricultural vinyl cover sheets, umbrellas, tents, etc.; of fluorescent whitening agents; and dyed textiles, etc.

2. Discussion of the Prior Art

It is commonly accepted that organic substances such as organic dyes tend to fade by the action of light. Extensive studies have been carried out in various technical fields including those for printing ink, textile dyeing as well as color photography, in an effort to improve the light fastness of organic dyes. The present invention is advantageously used to improve the light fastness of these organic substances.

In the following description of the invention, the term "organic substrate material" or "organic substrate" refers to materials appearing colored or colorless to human eye under the illumination of sunlight, as well as those having absorption peaks which lie in the infrared or in the ultraviolet region as in the case of optical whitening agents. In other words, the organic substrate materials of the present invention are organic materials (colorants and dyes) having their absorption peaks in the wavelength range of from 300 to 800 nm.

In the present specification, the term "dye" or "dyestuff" refers to an organic material which appears colored to the human eye under the illumination of sunlight. The term "light" conceptually involves electromagnetic radiation with wavelengths up to about 800 nm and, thus, includes ultraviolet rays below 400 nm, visible light of from about 400 nm to about 700 nm and infrared rays of from about 700 to about 800 nm.

It is widely known that organic substrate materials such as, for example, dyes and coloring agents, tend to fade under the influence of light irradiation. A number of technical reports dealing with methods of suppressing such tendency or of improving the light fastness of such materials are known. For example, U.S. Pat. No. 3,432,300 discloses that the light fastness of organic compounds such as indophenol, indoaniline, azo and azomethine dyes to visible and UV light is improved by the use of certain phenol derivatives containing a condensed heterocyclic structure. *The Theory of the Photographic Process*, authored by Mees et al, 3rd Ed. (1967) teaches in Chapter 17 that silver halide color photographic products generally give rise to azomethine or indoaniline dyes formed upon the reaction of the oxidation product of an aromatic primary amine developing agent and a color coupler. Also, various patents teach means to improve the stability to light of the color photographic images. Compounds which effectively improve the light fastness of the co-existing dye include, for example, the hydroquinone derivatives set forth in U.S. Pat. Nos. 2,360,290, 2,418,613, 2,675,314, 2,701,197, 2,704,713, 2,728,659, 2,732,300, 2,735,765, 2,710,801 and 2,816,028 and British Pat. No. 1,363,921, etc.; the gallic acid derivatives set forth in U.S. Pat. Nos. 3,457,079 and 3,069,262, Japanese Patent Publication No. 13496/1968, etc.; the p-alkoxyphenols set forth in U.S. Pat. Nos. 2,735,765 and 3,698,909; and the chroman and coumarane derivatives set forth in U.S. Pat. Nos. 3,432,300, 3,574,626, 3,574,627, 3,698,909, 3,573,050, 3,764,327 and 4,015,990, etc. These compounds are effective to prevent the fading or the discoloration of dye images by light to a certain but unsatisfactory extent.

British Pat. No. 1,451,000 discloses that the stability of organic substrate materials to light is enahnced by the use of azomethine quenching compounds which have their absorption peaks at a longer wavelength than the substrate material; unfortunately, the azomethine quenching compound is itself colored and adversely affects the color hue of the substrate material. Metal chelates can be used to prevent the degradation of polymeric substances caused by light as described in the following literature: J. P. Guillory and R. S. Becker, *J. Polym. Sci.*, Polym. Chem. Ed., 12, 993 (1974), and R. P. R. Ranaweera and G. Scott, *J. Polym. Sci.*, Polym. Lett. Ed., 13, 71 (1975), etc. Stabilization of dyes against light by the use of metal chelate is also discussed in U.S. Patent 4,050,938, Japanese Patent Application (OPI) No. 87649/1975 (The term "OPI" as used herein refers to a "published unexamined Japanese patent application") and Research Disclosure 15162 (1976). However, the disclosed metal chelates exhibit an unsatisfactory fade preventing effect and when the metal chelates are employed in a photographic emulsion for practical use, the disclosed metal chelates desensitize the silver halide probably due to an undesirable interaction with silver. Also, the metal chelates exhibit an undesirably poor solubility in common organic solvents. The latter drawback limits the working concentration of the chelate in the system and, thus, leads to an insufficient fade prevention. Moreover, these chelates cannot be present in a high concentration since they themselves are comparatively deeply colored, and adversely affect the color hue and the color purity of the dyes they are supposed to protect.

Furthermore, good fade preventing or light fastness improving agents for cyan dyes have not been known. While cyan dye images per se are generally color fast enough not to require any color fade preventing agent, using the present invention, cyan couplers or dyes having elaborate and highly developed structures would not be needed and inexpensive cyan dyes and couplers could be used, which is practically advantageous.

SUMMARY OF THE INVENTION

Accordingly, one principal object of the present invention is to provide a method of stabilizing organic substrate materials against the action of light.

Another object of the present invention is to provide a method of improving the stability of these materials against light without deteriorating the color hue as well as the color purity of organic substrate materials, in particular, organic dyes and coloring agents.

Still another object of the present invention is to provide a method of enhancing the stability of organic substrate materials against light by using stabilizing agents which are readily soluble in common organic solvents and which are highly compatible with various organic substrate materials.

Another object of the present invention is to disclose a method of improving the stability against light of dye images composing color photographs.

Another object of the present invention is to provide a method of improving the stability against the action of light of dyestuffs resulting from the reaction of a primary aromatic amine developing agent with a color coupler.

Still other objects of the present invention will become clear from the following detailed descriptions of the invention.

Another object of the present invention is to improve the light fastness of colored polymers Still another object of the present invention is to improve the light fastness of cyan dyes and cyan color photographic images.

DETAILED DESCRIPTION OF THE INVENTION

The above mentioned and other objects of the present invention have been achieved by making co-existant with an organic substrate material having an absorption peak between about 300 and 800 nm in wavelength, one compound represented by the following general formula (I):

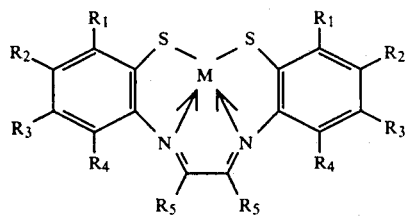

The terms "in the presence of" or "coexistant with" as used in the specification refer not only to coexistence of the substrate material and the compound of the formula (I) in the same solution, dispersion, emulsion or layer but also to the existence of the organic substrate and the complex in adjacent layers of a multilayered photographic material. As long as the complex compound is associated with the organic substrate material such that it improves the light fastness of the organic substrate, it is used "in the presence of" or "coexists" with the substrate for purposes of the present invention.

In the formula, M represents a metal atom selected from the group consisting of Cu, Co, Ni, Pd and Pt atoms. $R_1$, $R_2$, $R_3$ and $R_4$ each represents a hydrogen or halogen atom, a cyano group, or an alkyl, aryl, cycloalkyl, or heterocyclic group which may be substituted or unsubstituted and which may be attached directly to the carbon atom in the benzene ring or through a divalent connecting group. Alternatively, each of $R_1$ and $R_2$, $R_2$ and $R_3$, and $R_3$ and $R_4$ may combine to form the nonmetallic atom necessary to complete a 6-membered aromatic ring; and $R_5$ represents a hydrogen atom or a methyl group.

Halogen atoms represented by $R_1$, $R_2$, $R_3$ and $R_4$ include, for example, fluorine, chlorine, bromine and iodine atoms.

The alkyl groups represented by $R_1$, $R_2$, $R_3$ and $R_4$ are preferably straight or branched chained and substituted or unsubstituted having from 1 to 19 carbon atoms. The aryl groups represented by $R_1$, $R_2$, $R_3$ and $R_4$ are mono or bicyclic and preferably substituted or unsubstituted having from 6 to 14 carbon atoms.

Heterocyclic groups represented by $R_1$, $R_2$, $R_3$ and $R_4$ include 5- and 6-membered rings which may be substituted or unsubstituted.

Cycloalkyl groups represented by $R_1$, $R_2$, $R_3$ and $R_4$ include 5- and 6-membered rings which may be substituted or unsubstituted and include cyclopentyl and cyclohexyl groups.

The straight or branched chained alkyl group represented by $R_1$, $R_2$, $R_3$ and $R_4$ includes, for example, methyl, ethyl, propyl, butyl, hexyl, octyl, decyl, dodecyl, tetradecyl, hexadecyl, octadecyl, etc.

The aryl group represented by $R_1$, $R_2$, $R_3$ and $R_4$ includes, for example, phenyl and naphthyl.

The heterocyclic group represented by $R_1$, $R_2$, $R_3$ and $R_4$ is a 5- or 6-membered ring containing a nitrogen, oxygen or sulfur atom in the ring, including, for example, furyl, hydrofuryl, thienyl, pyrrolyl, pyrrolidyl, pyridyl, imidazolyl, pyrazolyl, quinolyl, indolyl, oxazolyl, thiazolyl, etc. The cycloalkyl group represented by $R_1$, $R_2$, $R_3$ and $R_4$ includes, for example, cyclopentyl, cyclohexyl, cyclohexenyl, cyclohexadienyl, etc.

The 6-membered aromatic ring completed by $R_1$ and $R_2$, $R_2$ and $R_3$ or $R_3$ and $R_4$ when they combine is represented by a benzene ring which may be substituted or unsubstituted, or further condensed with other ring structures. The 6-membered ring formed by combining $R_1$ with $R_2$, $R_2$ with $R_3$, or $R_3$ with $R_4$ includes, for example, benzene, naphthalene, isobenzothiophene, isobenzofuran and isoindoline nuclei, etc.

The alkyl, cycloalkyl, aryl or heterocyclic group represented by $R_1$, $R_2$, $R_3$ and $R_4$ may be bonded to the carbon atom in the ring of the compound characterizing the present invention through a divalent connecting group such as, for example, oxy (—O—), thio (—S—), amino, oxycarbonyl, carbonyl, carbonyloxy, carbamoyl, sulfamoyl, carbonylamino, sulfonylamino, and sulfonyl groups.

The substitution when an alkyl group represented by $R_1$, $R_2$, $R_3$ or $R_4$ is bonded to the carbon atom in the chelate ring through one of the above-cited divalent connecting group is exemplified by an alkoxy group (e.g., methoxy, ethoxy, butoxy, prooxy, n-decyloxy, n-dodecyloxy, or n-hexadecyloxy, etc.) in the case of the —O— connecting groups; an alkoxycarbonyl group (e.g., methoxycarbonyl, ethoxycarbonyl, butoxycarbonyl, n-decyloxycarbonyl, or n-hexadecyloxycarbonyl, etc.) in the case of an oxycarbonyl connecting group; an acyl group (e.g., acetyl, valeryl or stearyl, etc.) in the case of a carbonyl connecting group; an acyloxy group (e.g. acetoxy or hexadecylcarbonyloxy, etc.) in the case of a carbonyloxy connecting group; an alkylamino group (e. g., n-butylamino, N,N-diethylamino, N,N-didecylamino, etc.) in the case of an amino connecting group; an alkylcarbamoyl group (e.g., butylcarbamoyl, N,N-diethylcarbamoyl, n-dodecylcarbamoyl, etc.) in the case of a carbamoyl connecting group; an alkylsulfamoyl group (e.g., butylsulfamoyl, N,N-diethylsulfamoyl, n-dodecylsulfamoyl, etc.) in the case of a sulfamoyl connecting group; an alkylsulfonylamino group (e.g., methylsulfonylamino, butylsulfonylamino, etc.) in the case of a sulfonylamino connecting group; an alkylsulfonyl group (e.g., mesyl, ethanesulfonyl, etc.) in the case of a sulfonyl connecting group; or an acylamino group (e.g., acetylamino, valerylamino, palmitoylamino, etc.) in the case of a carbonylamino connecting group.

The substitution when a cycloalkyl group represented by $R_1$, $R_2$, $R_3$ and $R_4$ is bonded to the carbon atom in the chelate ring of the compound characterizing the present invention through one of the above-cited divalent connecting group is exemplified by cyclohexyloxy, cyclohexycarbonyl, cyclohexyloxycarbonyl, cyclohexylamino, cyclohexenylcarbonyl, and cyclohexenyloxy groups, etc.

The substitution when an aryl group represented by $R_1$, $R_2$, $R_3$ or $R_4$ is attached to the carbon atom in the chelate ring of the compound characterizing the present invention through one of the above-cited divalent connecting group is exemplified by an aryloxy group (e.g., phenoxy, naphthoxy, etc.), an aryloxycarbonyl group (e.g., phenoxycarbonyl, naphthoxycarbonyl, etc.), an acyl group (e.g., benzoyl, naphthoyl, etc.), an anilino group (e.g., phenylamino, N-methylanilino, N-acetylanilino, etc.), an acyloxy (e.g., benzoyloxy, toluoyloxy, etc.), an arylcarbamoyl group (e.g., phenylcarbamoyl, etc.), an arylsulfamoyl group (e.g., phenylsulfamoyl, etc.), an arylsulfonylamino group (e.g., phenylsulfonylamino, p-tolylsulfonylamino, etc.), an arylsulfonyl group (e.g., benzenesulfonyl, tosyl, etc.) or an arylcarbonylamino group (e.g., benzoylamino, etc.). $R_1$, $R_2$, $R_3$ and $R_4$ can be the same or different.

The alkyl, aryl, cycloalkyl and heterocyclic groups represented by $R_1$, $R_2$, $R_3$ and $R_4$ may have one or more substituents including the following: a halogen atom (Cl, Br, F, etc.), a cyano, a straight or branched chained alkyl group (e.g., methyl, ethyl, propyl, butyl, hexyl, octyl, decyl, dodecyl, tetradecyl, hexadecyl, heptadecyl, octadecyl, etc.), an aryl group (e.g., phenyl, tolyl, naphthyl, chlorophenyl, methoxyphenyl, acetylphenyl, etc.), an alkoxy group (e.g., methoxy, ethoxy, butoxy, propoxy, etc.), an aryloxy group (e.g., phenoxy, tolyloxy, naphthoxy, etc.), an alkoxycarbonyl group (e.g., methoxycarbonyl, butoxycarbonyl, etc.), an aryloxycarbonyl group (e.g., phenoxycarbonyl, tolyloxycarbonyl, etc.), an acyl group (e.g., formyl, acetyl, valeryl, stearoyl, benzoyl, toluoyl, naphthoyl, etc.), an acyloxy group (e.g., acetoxy, hexadecylcarbonyloxy, etc.), an acylamino group (e.g., acetamido, benzoylamido, etc.), an anilino group (e.g., phenylamino, N-methylanilino, N-phenylanilino, N-acetylanilino, etc.), an alkylamino group (e.g., n-butylamino, N,N-diethylamino, etc.), a carbamoyl group (e.g., n-butylcarbamoyl, N,N-diethylcarbamoyl, etc.), a sulfamoyl group (e.g., n-butylsulfamoyl, N,N-diethylsulfamoyl), n-dodecylsulfamoyl, etc.), an alkyl or arylsulfonylamino group (e.g., methylsulfonylamino, phenylsulfonylamino, etc.), and a sulfonyl group (e.g., mesyl, tosyl, etc.).

For the aforementioned alkyl, alkoxy, aryl, aryloxy, cycloalkyl and heterocyclic groups, the alkyl and aryl moieties thereof preferably contain 1 to 20 carbon atoms and 6 to 10 carbon atoms, respectively, as defined above for the primary substituent. Also, the alkyl groups are straight or branched chain and the aryl groups are mono or bicyclic.

Among the chelates represented by the general formula (I), those further defined by the following general formula (Ia) are particularly suited for the present invention.

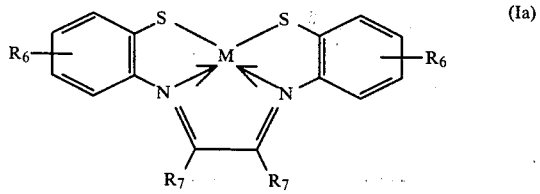

(Ia)

In the formula, M represents a metal selected from the group consisting of Cu, Co, Ni, Pd or Pt. $R_6$ represents a hydrogen or halogen atom, a substituted or unsubstituted alkyl, aryl, cycloalkyl or a heterocyclic group attached to the carbon atom in the benzene ring directly or through a divalent connecting group. $R_7$ represents a hydrogen atom or a methyl group.

The alkyl group represented by $R_6$ preferably contains from 1 to 19 carbon atoms, and may be straight or branched chain, and substituted or unsubstituted.

The aryl group represented by $R_6$, which may be substituted or unsubstituted, should preferably have from 6 to 14 carbon atoms.

The heterocyclic group represented by $R_6$ is preferably 5- or 6-membered, and may be substituted or unsubstituted.

The cycloalkyl group represented by $R_6$ is preferably 6- or 5-membered, and may be substituted or unsubstituted.

The straight or branched chain alkyl group represented by $R_6$ includes, for example, methyl, ethyl, propyl, butyl, hexyl, octyl, decyl, dodecyl, tetradecyl, hexadecyl, and octadecyl.

The aryl group represented by $R_6$ includes, for example, phenyl and naphthyl.

The heterocyclic group represented by $R_6$ which is a 5- or 6-membered one containing at least one nitrogen, oxygen or sulfur atom in the ring includes, for example, furyl, hydrofuryl, thienyl, pyrrolyl, pyrrolidyl, pyridyl, imidazolyl, pyrazolyl, quinolyl, indolyl, oxazolyl, thiazolyl, etc.

The cycloalkyl group represented by $R^6$ includes, for example, cyclopentyl, cyclohexyl, cyclohexenyl, or cyclohexadienyl, and the like.

Each of the above-cited alkyl, cycloalkyl, aryl and heterocyclic groups represented by $R_6$ may be attached to the carbon atom in the chelate ring of the compound characterizing the present invention by the aid of a divalent connecting group such as oxy (—O—), thio (—S—), amino, oxycarbonyl, carbonyl, carbonyloxy, carbamoyl, sulfamoyl, carbonylamino, sulfonylamino, sulfonyl, etc.

The substitution when an alkyl group represented by $R_6$ is attached to the carbon atom in the ring through one of the above-cited divalent connecting group is exemplified by an alkoxy group (e.g., methoxy, ethoxy, butoxy, propoxy, n-decyloxy, n-dodecyloxy, n-hexadecyloxy, etc.), an alkoxycarbonyl group (e.g., methoxycarbonyl, ethoxycarbonyl, butoxycarbonyl, n-decyloxycarbonyl, n-hexadecyloxycarbonyl, etc.), an acyl group (e.g., acetyl, valeryl, stearoyl, etc.), an acyloxy group (e.g., acetoxy, hexadecylcarbonyloxy, etc.), an alkylamino group (e.g., n-butylamino, N-N-diethylamino, N,N-didecylamino, etc.), an alkylcarbamoyl group (e.g., butylcarbamoyl, N,N-diethylcarbamoyl, n-dodecylcarbamoyl, etc.), an alkylsulfamoyl group (e.g., butylsulfamoyl, N,N-diethylsulfamoyl, n-dodecylsulfamoyl, etc.), a sulfonylamino group (e.g., methylsulfonylamino, butylsulfonylamino, etc.), a sulfonyl group (e.g., mesyl, ethanesulfonyl, etc.), and an acylamino group (e.g., acetylamino, valerylamino, palmitoylamino, etc.).

The substitution when a cycloalkyl group represented by $R_6$ is attached to the carbon atom in the ring of the compound characteristic of the present invention through one of the above-cited divalent connecting group is exemplified by the following group: cyclohexyloxy, cyclohexylcarbonyl, cyclohexyloxycarbonyl, cyclohexylamino, etc.

The subsituttion when an aryl group represented by $R_6$ is attached to the carbon atom in the ring of the compound characteristic of the present invention through one of the above-cited divalent connecting group is exemplified by the following groups: an aryloxy group (e.g., phenoxy, naphthoxy, etc.), an aryloxycarbonyl group (e.g., phenoxycarbonyl, naphthoxycarbonyl, etc.), an acyl group (e.g., benzoyl, naphthoyl, etc.), an acyloxy group (e.g., benzoyloxy, toluoyloxy, etc.), an anilino group (e.g., phenylamino, N-methylanilino, N-acetylanilino, etc.), an arylcarbamoyl group (e.g., phenylcarbamoyl, etc.), an arylsulfamoyl group (e.g., phenylsulfamoyl, etc.), and an arylcarbonylamino group (e.g., benzoylamino, etc.).

The alkyl, aryl, cycloalkyl and heterocyclic groups represented by $R_6$ delineated in detail hereinbefore may be substituted with the following substituent groups: a halogen atom (Cl, Br, F, etc.), a cyano group, a straight chain or branched chain alkyl group with from 1 to 20 carbon atoms (e.g., methyl, ethyl, propyl, butyl, hexyl, octyl, decyl, dodecyl, tetradecyl, hexadecyl, heptadecyl, octadecyl, etc.), an aryl group (e.g., phenyl, tolyl, naphthyl, chlorophenyl, methoxyphenyl, acetylphenyl, etc.), an alkoxy group (e.g., methoxy, ethoxy, butoxy, propoxy, etc.), an aryloxy group (e.g., phenoxy, tolyloxy, naphthoxy, etc.), an alkoxycarbonyl group (e.g., methoxycarbonyl, butoxycarbonyl, etc.), an aryloxycarbonyl group (e.g., phenoxycarbonyl, tolyloxycarbonyl, etc.), an acyl group (e.g., formyl, acetyl, valeryl, stearoyl, benzoyl, toluoyl, naphthoyl, etc.), an acyloxy group (e.g., acetoxy, hexadecylcarbonyloxy, etc.), an acylamino group (e.g., acetamido, benzoylamido, etc.), an anilino group (e.g., phenylamino, N-methylanilino, N-phenylanilino, N-acetylanilino, etc.), an alkylamino group (e.g., n-butylamino, N,N-diethylamino, etc.), a carbamoyl group (e.g., n-butylcarbamoyl, N,N-diethylcarbamoyl, etc.), a sulfamoyl group (e.g., n-butylsulfamoyl, N,N-diethylsulfamoyl, n-dodecylsulfamoyl, etc.), a sulfonylamino group (e.g., methylsulfonylamino, phenylsulfonylamino, etc.), and a sulfonyl group (e.g., mesyl, tosyl, etc.).

The following compounds are listed for the purpose of illustrating particularly suited ones for practicing the present invention. All of them fall in the category defined by the general formula (I).

| Compound No. | M | $R_1$* | $R_2$* | $R_3$* | $R_4$* | $R_5$ |
|---|---|---|---|---|---|---|
| I-1 | Ni | H | H | H | H | H |
| I-2 | Ni | H | H | H | H | $CH_3$ |
| I-3 | Ni | H | $n-C_4H_9$ | H | H | H |
| I-4 | Ni | H | $n-C_4H_9$ | H | H | $CH_3$ |
| I-5 | Ni | H | $CH_3O$ | H | H | H |
| I-6 | Ni | H | $CH_3O$ | H | H | $CH_3$ |
| I-7 | Ni | $CO_2CH_3$ | H | H | H | $CH_3$ |
| I-8 | Ni | $CO_2n-C_8H_{17}$ | H | H | H | $CH_3$ |
| I-9 | Ni | $CO_2n-C_{16}H_{33}$ | H | H | H | H |
| I-10 | Ni | $CO_2n-C_3F_7$ | H | H | H | H |
| I-11 | Ni | $CO_2n-C_3F_7$ | H | H | H | $CH_3$ |
| I-12 | Ni | H | H | H | $CO_2n-C_{10}H_{21}$ | H |
| I-13 | Ni | H | H | H | $CO_2n-C_{10}H_{21}$ | $CH_3$ |
| I-14 | Ni | H | H | $CH_2O_2Cn-C_{10}H_{21}$ | H | H |
| I-15 | Ni | H | H | $CH_2O_2Cn-C_{10}H_{21}$ | H | $CH_3$ |
| I-16 | Ni | H | H | $SO_2NHn-C_8H_{17}$ | H | H |
| I-17 | Ni | H | H | $SO_2NHn-C_8H_{17}$ | H | $CH_3$ |
| I-18 | Ni | H | H | $NHCOn-C_{12}H_{25}$ | H | H |
| I-19 | Ni | H | H | $NHCOn-C_{12}H_{25}$ | H | $CH_3$ |
| I-20 | Ni | H | H | $CH=N-n-C_8H_{17}$ | H | $CH_3$ |
| I-21 | Ni | H | $CO_2n-C_4H_9$ | H | $CH_3$ | H |
| I-22 | Ni | H | Cl | H | $CO_2n-C_{10}H_{21}$ | H |
| I-23 | Ni | H | $CH_3$ | H | $CH_3$ | $CH_3$ |
| I-24 | Ni | H | H | $CH_3$ | $CH_3$ | H |
| I-25 | Ni | $CH_3$ | H | H | $CH_3$ | $CH_3$ |
| I-26 | Ni | Cl | Cl | Cl | Cl | H |
| I-27 | Cu | $CO_2n-C_{16}H_{33}$ | H | H | H | H |
| I-28 | Co | $CO_2n-C_{16}H_{33}$ | H | H | H | H |
| I-29 | Pd | $CO_2n-C_{16}H_{33}$ | H | H | H | H |
| I-30 | Pt | $CO_2n-C_{16}H_{33}$ | H | H | H | H |

I-31

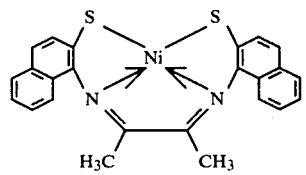

I-32

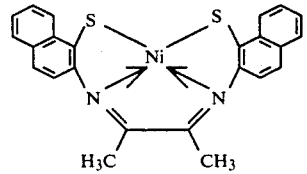

*including connecting group

The synthesis procedures for these chelate compounds are given in, for example, the following: E.

Bayer, *Angew. Chem.*, 73, 659 (1961), and Q. Fernands, H. Frieser, *J.A.C.S.*, 86, 3056 (1964). Basically, benzothiazoline derivatives which are obtained by reacting o-aminothiophenol derivatives and α-diketones are heated in the presence of metal acetates in an alcohol solvent under reflux. After refluxing for 1 hour, the reaction mixture is allowed to stand overnight in a refrigerator. The resulting precipitate is separated, recrystallized, if necessary, and dried in a conventional manner.

SYNTHESIS EXAMPLE 1

Compound I-2

75 g of 2-aminothiophenol was dissolved in 200 ml methanol, to which 18 g biacetyl was added dropwise. The reaction mixture was refluxed for one-half hour under heating and allowed to cool overnight. White 2,2'-dimethyl-2,2'-bisbenzothiazoline crystals formed. This product was separated by filtration, washed with methanol and dried under reduced pressure. 8.5 g of the crystals was dissolved in 100 ml methanol and refluxed. To this solution was added dropwise a solution comprising 7 g of nickel acetate tetrahydrate dissolved in 200 ml methanol. After another hour reflux, the reaction mixture was left to cool overnight. The chelate compound precipitated as fine crystals, which were rinsed with a small volume of dioxane, and then with methanol thoroughly. The purified product was dried under reduced pressure.

SYNTHESIS EXAMPLE 2

Compound I-4

To a solution prepared by dissolving 94 g of 5-n-butyl-2-aminothiophenol in 200 ml methanol, 8.6 g biacetyl was added dropwise and refluxed for one-half hour. After evaporating the reaction mixture to half the volume, it was allowed to cool overnight. A bis-benzothiazoline derivative was crystallized and separated by filtration, rinsed with a small amount of cold methanol and dried under reduced pressure.

5 g of the thus-separated crystals were dissolved in 50 ml methanol. While refluxing this solution, another solution comprising 1.9 g nickel acetate tetrahydrate dissolved in 80 ml methanol was added dropwise. After the completion of this addition, refluxing was continued for another hour. After the addition of 50 ml ether, the reaction vessel was allowed to cool overnight. The resulting crystals were collected by filtration, washed with ether and dried under reduced pressure.

The organic substrate material of the present invention includes all the dyestuffs belonging to various groups classified from the viewpoint of textile dyeing: i.e., water-soluble dyes such as basic, acid, direct, water-soluble vat and mordant dyes, etc.; water-insoluble dyes such as sulfur, vat, oil-soluble, dispersion, azoic, and oxidative dyes, etc.; and reactive dyes. Not only compounds which appear colored under the illumination of sunlight, but also colorless or pale yellow compounds such as fluorescent whitening agents are within the meaning of organic substrate materials defined in the present invention.

Dyes which are particularly suited for the application of the present invention include quinoneimine dyes (e.g., azine, oxazine, or thiazine dyes, etc.), methine or polymethine dyes (e.g., cyanine, azomethine, and other dyes), azo dyes, azomethine dyes, anthraquinone dyes, indamine dyes, indophenol dyes, indigoid dyes, carbonium dyes, formazane dyes, etc., classified according to chemical structure.

The organic substrate material associated with the present invention includes the dyes making up photographic images including, for example, those resulting from the reaction of a color coupler, a DRR (dye releasing redox) compound, a DDR (dye developer releasing) coupler, an aminolazone derivative, dye developer, etc., and those used for silver dye bleach process, etc.

More specifically, anthraquinone, quinoneimine, azo, methine, polymethine, indamine, indophenol and formazane type dyes are particularly suited for the application of the present invention. Even more favorable are methine and polymethine type dyes, and indamine and indophenol dyes, all of which have in their chemical structure the following moiety.

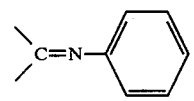

The phenyl group in the above expression may be substituted with an alkyl group, an alkoxy group or an amino group or with a halogen atom, etc.

The aforementioned dye forming couplers include those capable of providing yellow, cyan and magenta dyes. Such couplers may be so-called 4-equivalent or 2-equivalent type couplers disclosed in, for example, U.S. Pat. Nos. 3,277,155 and 3,458,315.

Generally, yellow dye forming couplers have at least one methylene group activated by a carbonyl group (e.g., an open-chain ketomethylene group), including β-diketone, β-ketoacylamide groups such as benzoylacetanilide and α-pivalylacetanilide. This type of coupler is exemplified by U.S. Pat. Nos. 2,428,054, 4,026,706, 2,499,966, 2,453,661, 2,778,658, 2,908,573, 3,227,550, 3,253,924, 3,277,155 and 3,384,657 and British Pat. No. 503,752.

Magenta dye forming couplers are exemplified by 5-pyrazolone derivatives. This type of coupler is disclosed in, for example, U.S. Pat. Nos. 2,600,788, 2,725,292, 2,908,573, 3,006,759, 3,062,653, 3,152,896, 3,227,550, 3,252,924, 4,026,706 and 3,311,476.

Other types of magenta dye forming couplers are indazolone derivatives as set forth in Vittum & Weissberger, *Journal of Photographic Science*, 6 (1958), p. 158; and U.S. Pat. No. 3,061,432 discloses pyrazolinobenzimidazole compounds. Also included are pyrazolo-s-triazoles set forth in Belgian Pat. No. 724,427 and 2-cyanoacetylcoumarone set forth in U.S. Pat. No. 2,115,394.

Cyan dye forming couplers include phenol and α-naphthol derivatives which form indaniline dyestuffs by reacting with the oxidized color developing agent. Such derivatives are disclosed in U.S. Pat. Nos. 2,275,292, 2,423,730, 2,474,293, 2,895,826, 2,908,573, 3,043,892, 4,026,706, 3,227,550 and 3,253,294.

General descriptions of these and other coupler compounds are also found in, for example, *Encyclopedia of Chemical Technology*, authored by Kirk and Othmer, Vol. 5, pp. 822–825, and *Photographic Chemistry*, authored by Grafkides, Vol. 2, pp. 596–614.

As has been pointed out above, the method of the present invention may be practiced on dyes obtained from such couplers upon the reaction thereof with the oxidation product of a primary aromatic amine developing agent. Such developing agents include aminophenol as well as phenylenediamine, which can be used individually or in mixed forms.

Typical developing agents which can react with various couplers to give organic substrate materials of the present invention include the following.

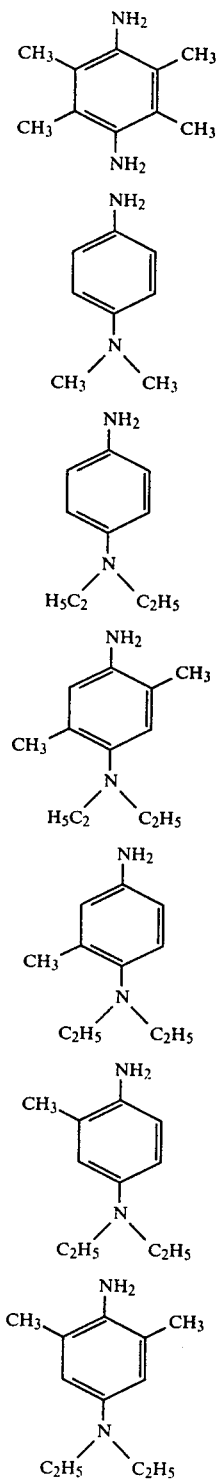

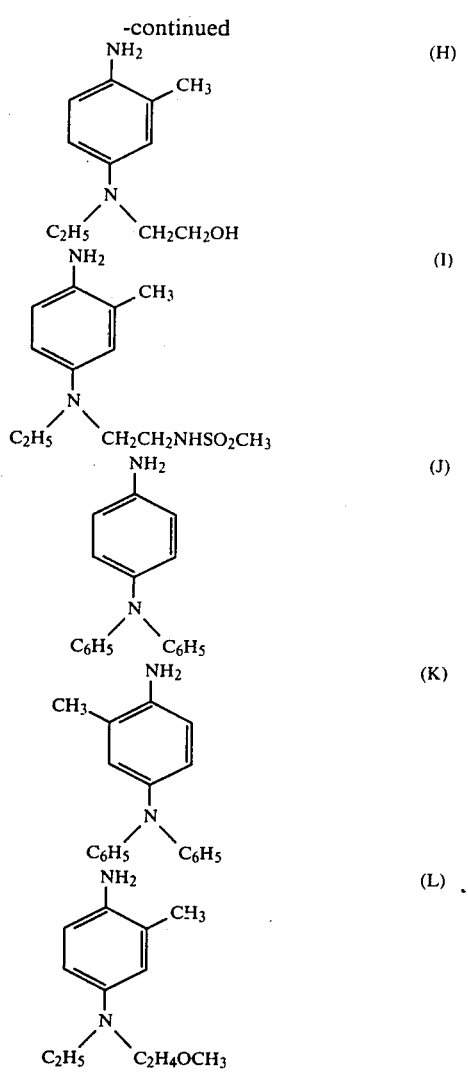

The developing agents illustrated above and others which can provide organic substrate materials upon the reaction with color couplers, cyan, magenta and yellow color couplers which are preferably employed are represented by the formula (IIa), (IIb) or (IIc), respectively:

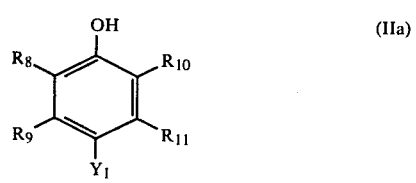

wherein $R_8$, $R_9$, $R_{10}$ and $R_{11}$ each represents a hydrogen atom, a halogen atom (e.g., fluorine, chlorine, bromine or iodine), an alkyl group having 1 to 20 carbon atoms (hereinafter, all of the alkyl groups referred to with respect to formulae (IIa), (IIb), and (IIc) may possess 1 to 20 carbon atoms) (e.g., methyl, ethyl, octyl, dodecyl, tetradecyl, octadecyl, etc.); alkyl or aryl substituted carbamoyl wherein the aryl moiety has 6 to 10 carbon atoms (hereafter all of the aryl groups referred to with respect to formulae (IIa), (IIb) and (IIc) may possess 6 to 10 carbon atoms) (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an amido group (e.g., acetamido, butylamido, benzamido, phenacetamido, etc.); a sulfonamido group (e.g., benzenesulfonylamino), a phosphoric acid amido group, a ureido group, etc.).

$R_8$ and $R_9$ may combine with each other to form a 6-membered carbocyclic ring (e.g., a benzene ring which may further be substituted with an alkyl or aryl group).

$Y_1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms, hereafter also the same; an aryloxy group wherein the aryl moiety has 6 to 10 carbon atoms, hereafter the same; a sulfonamido group, a sulfonyl group, a carbamoyl group, an imido group, an aminosulfonyloxy group, an alkylcarbonyloxy group, an arylcarbonyloxy group, an alkylthio group, an arylthio group, a hetero ring thio group, etc.), the details of which are well known in the art.

The alkyl, carbamoyl, sulfamoyl and amido groups expressed by $R_8$, $R_9$, $R_{10}$ and $R_{11}$, or the 6-membered ring formed by combining $R_8$ and $R_9$ with each other can also be substituted with other substituents, for example, an alkyl group (e.g., methyl, ethyl, propyl, octyl, dodecyl, tetradecyl, octadecyl, etc.); an aryl group (e.g., phenyl, tolyl, naphthyl, etc.); an aryloxy group (e.g., phenoxy, 2,5-di-(t)-amylphenoxy, etc.); a halogen atom (e.g., chlorine, bromine, fluorine, etc.); and the like.

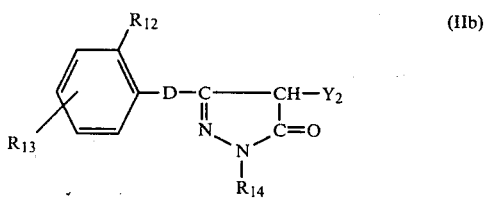

(IIb)

wherein $R_{12}$ represents a hydrogen atom, a halogen atom (e.g., chlorine, bromine, fluorine, etc.); an alkyl group (e.g., methyl, ethyl, n-propyl, etc.); or an alkoxy group (e.g., methoxy, ethoxy, etc.); $R_{13}$ represents an alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group (e.g., decylcarbamoyl, tetradecylcarbamoyl, octadecylcarbamoyl, etc.); an N-alkylsulfamoyl group (e.g., decylsulfamoyl, tetradecylsulfamoyl, octadecylsulfamoyl, etc.); an alkoxycarbonyl group (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc.; and $R_{14}$ represents an aryl group (e.g., phenyl, naphthyl, etc., said alkyl and aryl groups having the number of carbon atoms discussed above with respect to formula (IIa)). D represents an amino group, a carbonylamino group, or a ureido group. $Y_2$ represents a hydrogen atom, a halogen atom (e.g., chlorine, bromine, etc.); or a group which is releasable upon reaction with the oxidation product with a developing agent (e.g., an arylazo group, an aryloxy group, an acyloxy group, an alkylthio group, an arylthio group, etc.), Such groups are well known.

The alkyl or alkoxy group represented by $R_{12}$, the alkyl, amido, N-alkylcarbamoyl, N-alkylsulfamoyl, alkoxycarbonyl or acyloxy group represented by $R_{13}$, or the aryl group represented by $R_{14}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

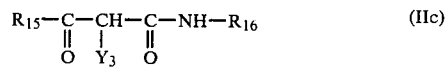

(IIc)

wherein $R_{15}$ represents an alkyl group (e.g., methyl, ethyl, (t)-butyl, (t)-octyl, etc.) or an aryl group (e.g., phenyl); and $R_{16}$ represents an aryl group (e.g., phenyl); $Y_3$ represents a hydrogen atom, a halogen atom (e.g., chlorine, bromine, etc.), or a group which is releasable upon the reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group; which are well known in the art.

The alkyl or aryl group represented by $R_{15}$ and the aryl group represented by $R_{16}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc.

The following couplers are illustrative, however, they are not to be construed as limiting the present invention.

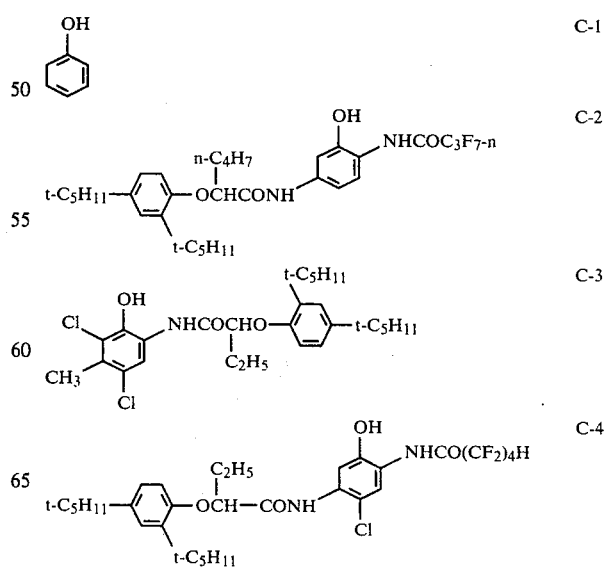

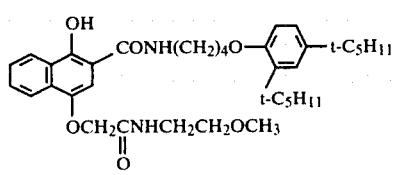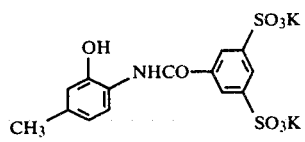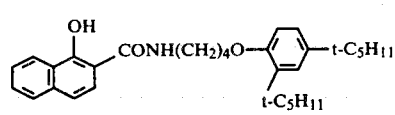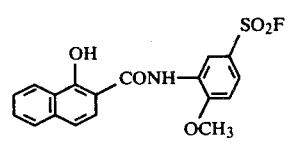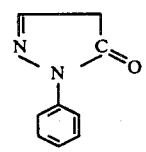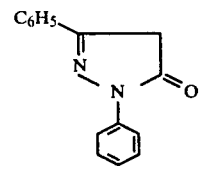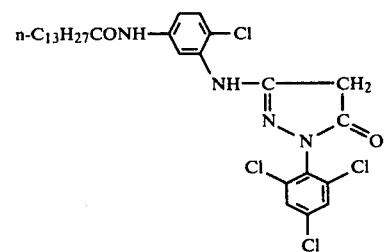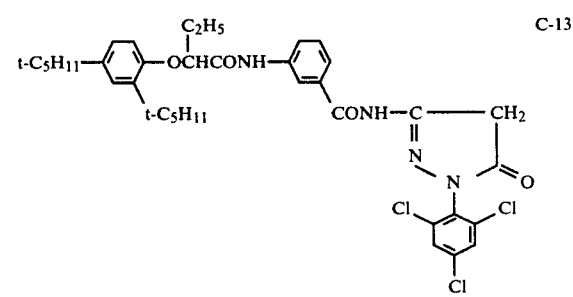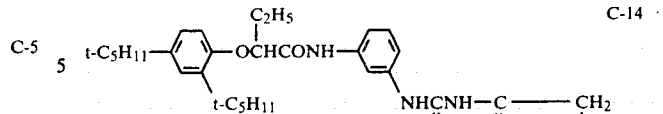

-continued
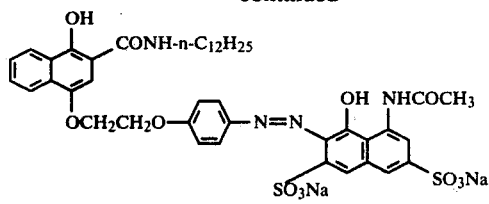
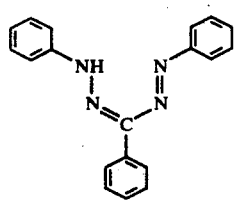
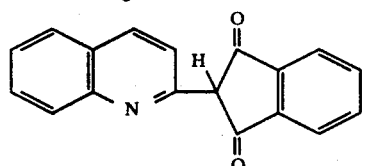
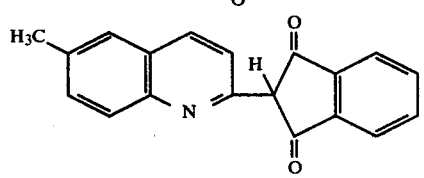
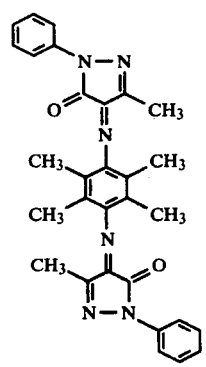
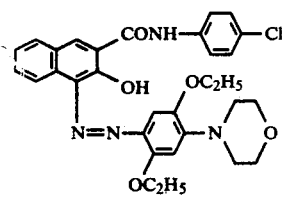
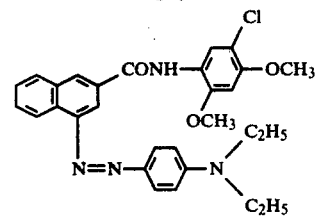
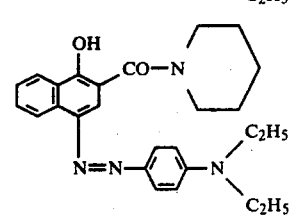
-continued
C-23
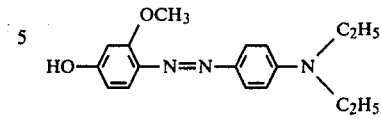
C-31
C-24
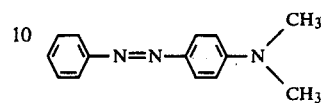
C-32
C-25
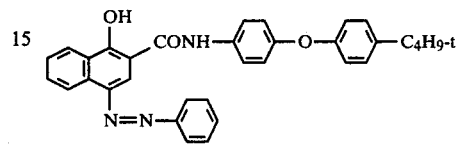
C-33
C-26
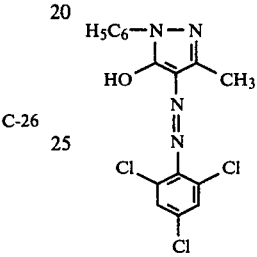
C-34
C-27
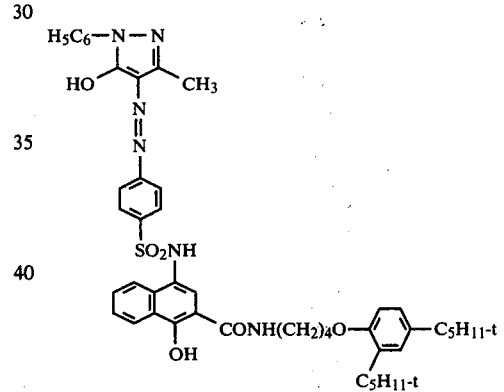
C-35
C-28
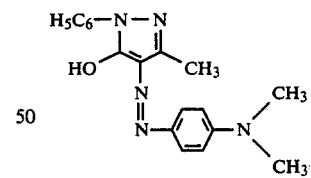
C-36
C-29
C-37
C-30
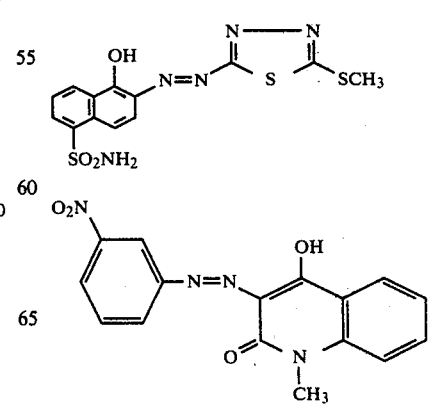
C-38

-continued
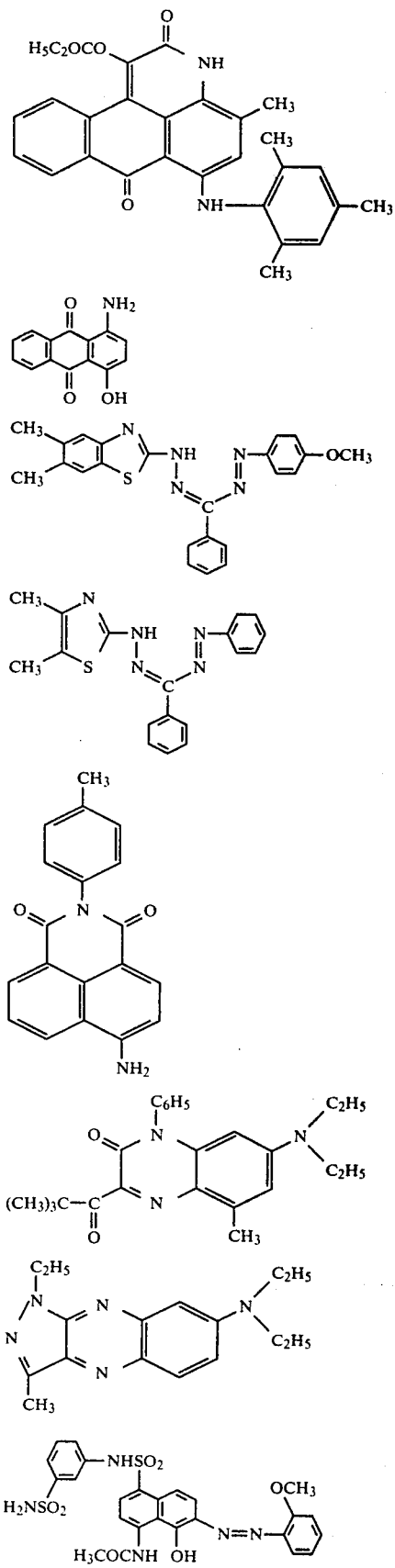
-continued
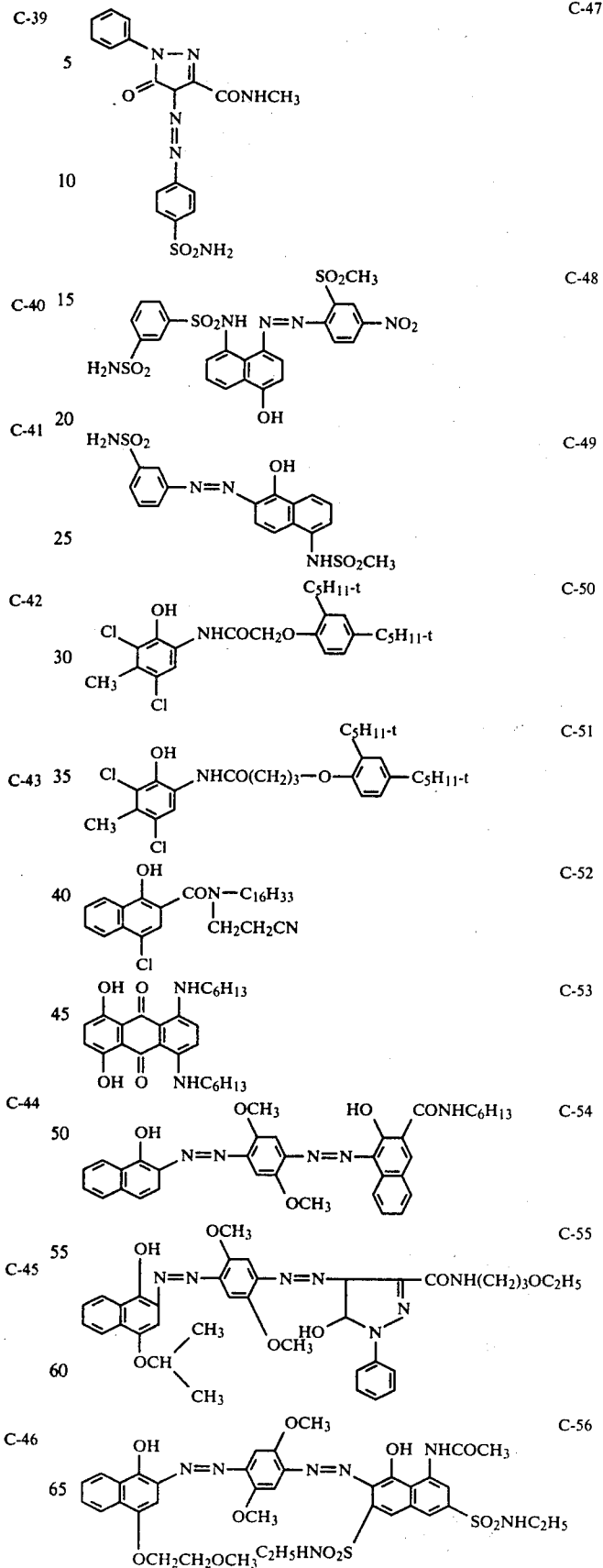

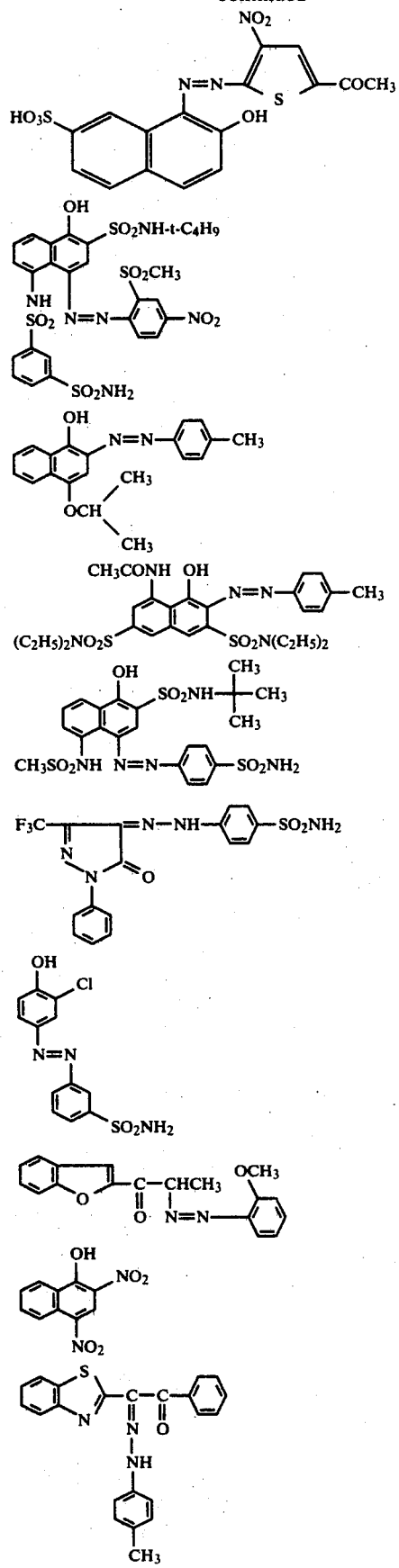

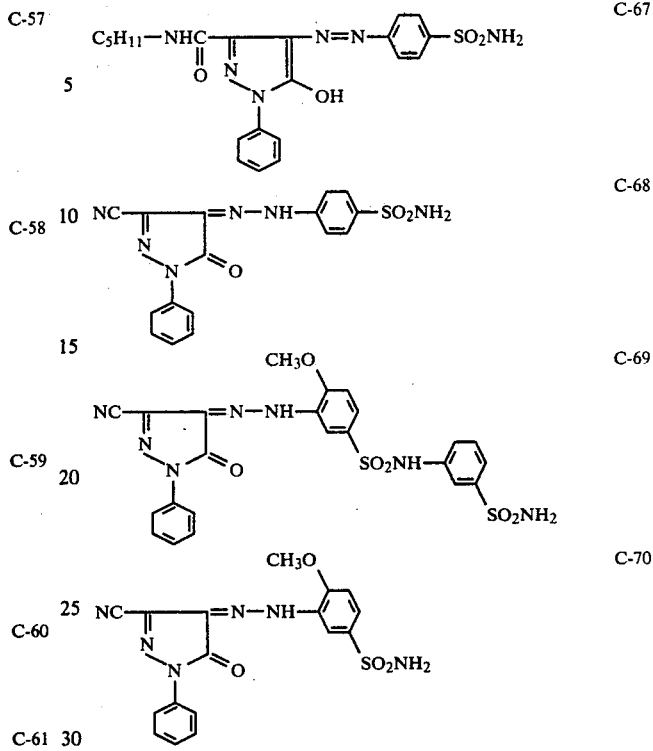

Still other types of dyes to which the present invention can be preferably applied include those which are formed by the oxidation of a DRR compounds described in the following patents and disclosure: U.S. Published Application B-351,673, U.S. Pat. Nos. 3,932,381, 3,928,312, 3,931,144, 3,954,476, 3,929,760, 3,942,987, 3,932,380, 4,013,635 and 4,013,633, Japanese Patent Application (OPI) Nos. 113624/1976, 109928/1976, 104343/1976 and 4819/1977, Japanese Patent Application No. 64533/1977 (corresponding to OPI No. 149328/78), "Research Disclosure" (1976 November), pp. 68–74, No. 13024, etc.

Also, the present invention is applicable to those dyes that are released or formed as a result of reaction between a DDR coupler and the oxidation product of a color developing agent; such DDR couplers are disclosed in, for example, British Pat. Nos. 840,731, 904,364, 932,272, 1,014,725, 1,038,331, 1,066,352 and 1,097,064, Japanese Patent Application (OPI) No. 133021/1976, U.S. Defensive Publication No. T900,029, U.S. Pat. No. 3,227,550, etc.

The present invention is also applicable to dye developers set forth in Japanese Patent Publication Nos. 182/1960, 18332/1960, 32130/1973, 43950/1971 and 2618/1974, etc.

Still other types of dyes to which the present invention is applicable include those employed in the silver dye bleach process. Such yellow dyes are exemplified by azo dyes such as Direct Fast Yellow GC (C.I. 29000), Crysophenine (C.I. 24895), etc., benzoquinone dyes such as Indigo Golden Yellow IGK (C.I. 59101), Indigosol Yellow 2GB (C.I. 68420), Mikethrene Yellow GC (C.I. 67300), Indanthrene Yellow 4GK (C.I. 68405), Argosol Yellow GCA-CF (C.I. 67301), Indanthrene Yellow GF (C.I. 68420), etc., anthraquinone dyes, soluble vat dyes with fused ring structures, other types of vat dye, etc. Magenta dyes are exemplified by azo dyes such as Sumilite Supra Rubinol B (C.I. 29225), Benzobrilliant Gelanine B (C.I. 15080), etc. Indigoid dyes are exemplified by dyes such as Indigosol Brilliant Pink IR (C.I. 73361), Indigosol Violet 15R (C.I. 59321), Indigosol Red Violet IRRL (C.I. 59316), Indanthrene Red Violet RRK (C.I. 67895), Mikethrene Brilliant Violet BBK (C.I. 6335), etc., soluble vat dyes comprising anthraquinone-hetero-polycyclic compounds, and still other types of vat dyes. Cyan dyes include azo dyes such as Direct Sky Blue 6B (C.I. 24410), Direct Brilliant Blue 2B (C.I. 22610), Sumilite Supra Blue (C.I. 34200), etc., phthalocyanine dyes such as Sumilite Supra Turkeys Blue G (C.I. 74180), Mikethrene Brilliant Blue 4G (C.I. 74140), etc., Indanthrene Turkeys Blue 5G (C.I. 69845), Indanthrene Blue GCD (C.I. 73066), Indigosol 04G (C.I. 73046), Anthrasol Green IB (C.I. 59826), etc.

The metal chelate complex associated with the present invention acts to stabilize organic substrate materials to color fading, and can be incorporated in at least one layer making up the emulsion coatings of a color photographic film product.

The organic substrate material and the complex can be present in one or more of the hydrophilic colloid layers of a color photographic element. It is preferred that the metal chelate complex and the organic substrate material be present (i.e., coexist) in the same emulsion layer, of course, the effect of the present invention can also be attained when the complex and substrate are present in contiguous layers inasmuch as diffusion is allowed to occur between the layers. Were any (further) undesirable diffusion to occur, conventional mordanting techniques could be applied to the present invention. The substrate and complex can be present in non-light-sensitive elements as well, such as the dye image-receiving member of a photographic diffusion transfer film unit. In the case of image transfer units, the metal chelate complex is preferably located in a layer where dye images are finally found, i.e., in an image-receiving layer. Usually, the dye images formed in the image-receiving layer do not diffuse further into any other layer(s) so the complex is generally used in the image-receiving layer. When the substrate material and the complex are contained in such a non-light-sensitive image-recording element, they are preferably mordanted. In such a case, the chelate complex possesses a ligand capable of holding the complex in the mordanted layer of the image-receiving element so that the complex does not diffuse and leave the vicinity of the dye substrate to be stabilized. However, using the mordanting techniques effectively, the chelate complex can be incorporated in any other layer adjacent the image-receiving layer, as long as diffusion is effected and the chelate complex interacts with the dye images to improve light fastness.

Various types of image transfer film units can be designated as well suited for practicing the present invention. One is the imbibition transfer film unit set forth in U.S. Pat. No. 2,882,156. The present invention can further be applied to the color image transfer film units described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Pat. Nos. 757,959 and 757,960.

Efficient methods of dispersing these metal chelates include those known and employed for the dispersion of couplers. U.S. Pat. Nos. 2,304,939 and 2,322,027 disclose the use of low volatile organic solvents for the dissolution of metal chelates. Other methods applicable for the purpose include those described in U.S. Pat. Nos. 2,801,170, 2801,171 and 2,949,360 wherein low-boiling point of water-soluble organic solvents are employed in conjunction with low-volatile solvents.

Low-volatile solvents suitable for the dispersion of the organic substrate materials as well as the metal chelate involved in the present invention include di-n-butyl phthalate, benzyl phthalate, triphenyl phosphate, tri-o-cresyl phosphate, diphenylmono-p-tert-butylphenyl phosphate, monophenyl-di-p-tert-butylphenyl phosphate, diphenylmono-o-chlorophenyl phosphate, monophenyl-di-o-chlorophenyl phosphate, 2,4-di-n-amylphenol, 2,4-di-t-amylphenol, N,N-diethyllaurylamide, trioctyl phosphate, and trihexyl phosphate, all of which are set forth in U.S. Pat. No. 3,676,137.

Readily volatile and/or water-soluble organic solvents which can be used in conjunction with the above-cited low volatile solvents are those described in, for example, U.S. Pat. Nos. 2,801,171, 2,801,170 and 2,949,360, including: (1) Solvents which are substantially immiscible with water such as methyl acetate, ethyl acetate, propyl acetate, butyl acetate, isopropyl acetate, ethyl propionate, sec-butyl alcohol, ethyl formate, butyl formate, nitromethane, carbon tetrachloride, chloroform, etc., and (2) Water-miscible organic solvents such as, for example, methyl isobutyl ketone, $\beta$-ethoxyethyl acetate, $\beta$-butoxytetrahydrofurfuryl adipate, diethylene glycol monoacetate, methoxytriglycol acetate, acetonylacetone, diacetone alcohol, ethylene glycol, diethylene glycol, dipropylene glycol, acetone, methanol, ethanol, acetonitrile, dimethylformamide, dioxane, etc.

The complex compound and the substrate material embodying the invention can be used together with the materials described in *Product Licensing Index*, Vol. 92, No. 9232 (1971, December), pp. 107–110 according to the methods also described therein. Reference is made to Chapters I, II, III, IV, V, VII, VIII, IX, X, XI, XII, XIII, XIV, XV, XVI, XVII, XVIII and XXIII.

In general, the complex of the formula (I) is dissolved or suspended in an appropriate solvent which is chosen, depending upon the physical properties of the complex used, from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds; solutions and/or dispersions may be prepared separately and subsequently mixed. For example, a fluorescent whitening agent may be dissolved or suspended in an organic or inorganic solvent such as water or dimethylformamide, etc., together with the complex of the present invention or separately; and the mixture may be coated onto or incorporated into a suitable base substance. An adjacent double layer coating is possible and, in some cases, may be preferred if some diffusion between the contiguous layers occurs and light fastness improvement is effected. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

The colored polymer as used herein is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468.

Any addition of the complex will bring about an improvement in the light fastness of the substrate to some extent, and theoretically there is no upper limit on the amount of the complex which may be added. Preferably, the complex is present in an amount of at least 0.1 mol% based on 1 mol of the organic substrate material, more preferably, in an amount of 0.1 to 1,000 mol%, and most preferably, in an amount of 1 to 300 mol%. In the case of a photographic material, the amount is often expressed in a weight unit per square meter of photographic material which can be calculated from the parameters set out above. For convenience, however, in the case of a photographic material, the complex is preferably present in an amount of at least one micromol per square meter of the photographic product, and more preferably, in an amount of from about 10 to $1 \times 10^4$ micromols per square meter of the product.

The concentration of the organic substrate material corresponds, in general, to that for the image forming material usually used in color photographic technology. As is well known to those skilled in the art, the organic substrate material is preferably present in the range of from about 10 to $10^4$ micromols per square meter of the photographic product and a more preferable range is from about 100 to about $3 \times 10^3$ micromols per square meter of the photographic product.

The substrate material involved in the present invention usually has the absorption peak at a wavelength shorter than about 800 nm. This peak should preferably be in the range of from about 300 to 800 nm, and more preferably, from about 400 to 800 nm.

Any type of support material ordinarily employed in photographic products can be used in the present invention, including, for example, cellulose nitrate film, cellulose acetate film, cellulose acetate-butyrate film, cellulose acetate-propionate film, polystyrene film, poly(ethylene terephthalate) film, polycarbonate film, laminated sheet products comprising the above-mentioned films, paper, etc. Especially suitable are baryta coated paper, paper laminated or coated with an α-olefin polymer such as polyethylene, polypropylene and the like comprising $C_2$–$C_{10}$ α-olefins, those plastic films that are disclosed in Japanese Patent Publication No. 19068/1972 which are provided with a roughened surface of an improved adhesive property to different polymeric materials, etc.

To prepare a photographic light-sensitive material for the present invention, various hydrophilic colloids are employed. Hydrophilic colloid materials used as the binder for the photographic emulsion coating and/or other additional coatings include, for example, gelatin, colloidal albumin, casein, cellulose derivatives such as carboxymethyl cellulose, hydroxyethyl cellulose, etc., carbohydrate derivatives such as agar-agar, sodium alginate, starch and its derivatives, etc., synthetic hydrophilic polymers such as poly(vinyl alcohol), poly(N-vinylpyrrolidone), acrylic acid containing copolymers, maleic anhydride copolymers, polyacrylamide, derivatives from these synthetic polymers including partially hydrolized products thereof, etc. If necessary, two or more of these colloidal materials are used simultaneously provided that they are mutually compatible.

Among these, most extensively used is gelatin, which can be replaced totally or partially with synthetic polymeric materials or with so-called gelatin derivatives. Such gelatin derivatives can be prepared by modifying or treating gelatin with reagents which have a functional group capable of reacting with the reactive groups contained in the gelatin molecule such as amino, imino, hydroxy or carboxy groups, or by grafting to the gelatin molecular chain a suitable synthetic polymer chain.

The photographic emulsion coating or other additional coatings composing the photographic product used for the present invention can involve synthetic polymer materials such as, for example, a latex of vinyl polymer dispersed in water and those which can improve the dimensional stability of the final product. The photographic product can contain one or more of such polymeric materials, and in some cases, a hydrophilic, water-permeable colloid.

Silver halide photographic emulsions useful in conjunction with the present invention are usually prepared by mixing an aqueous solution of a water-soluble silver salt (e.g., silver nitrate) with an aqueous solution of a water-soluble halide salt (e.g., potassium bromide) in the presence of a water-soluble polymeric material such as gelatin. The resulting silver halide includes not only silver chloride and silver bromide, but those containing halogen mixtures such as chlorobromide, iodobromide, chloroiodobromide, etc. Any method well known in the art can be adopted to prepare grains of such a silver halide, self-evidently including single and double jet methods, control double jet method, etc. One can also blend two or more kinds of silver halide photographic emulsion each of which has been prepared independently.

A number of additives can be incorporated into the photographic emulsion in order to prevent deterioration of photographic speed or the generation of fog during the manufacturing operations, the storage period and photographic processing. Such additives include various heterocyclic compounds such as 4-hydryoxy-6-methyl-1,3,3a,7-tetrazaindene, 3-methylbenzothiazole, 1-phenyl-5-mercaptotetrazole, etc., Hg containing compounds, mercapto compounds, metal salts, etc.

The photographic emulsion used in the present invention can be chemically sensitized according to one of the known methods. Chemical sensitizers include gold compounds such as chloroaurates, gold trichloride, etc., salts of noble metals such as Pt, Pd, Ir, Rd, etc., those sulfur compounds that can react with silver salts to yield silver sulfide (e.g., sodium thiosulfate), and other reducing substances such as stannous salt, amine, etc.

The photographic emulsion used in the present invention can be spectrally sensitized or supersensitized by using cyanine dyes such as cyanine, merocyanine, carbocyanine, individually or assortedly among themselves or with styryl type dyes. The selection of dyes depends on the spectral region to be sensitized, the degree of spectral sensitivity, etc., which vary with the expected application of the resulting product.

The hydrophilic colloid contained in the photographic material used in the present invention can be, if desired, cross-linked with a variety of hardening agents such as, for example, aldehydes, active halogen compounds, vinylsulfones, carbodiimides, N-methylol compounds, epoxy compounds, etc.

According to one embodiment of the present invention where the method of the invention is applied to a color photographic product, the color photographic material is, after exposed imagewise processed in an ordinary manner to provide color images. Such processing comprises color development, bleach and fix, to which other steps such as rinse with water or stabilization may be introduced, if necessary. Some of these processing operations can be united into a mono-bath step, a typical example of which is the so-called "blix" operation comprised of bleach and fix. The color development is carried out in an alkaline solution containing an aromatic primary amine developing agent. Preferable compounds useful as the developing agent include Compounds (A) to (L) already illustrated in the specification.

In one embodiment, the present invention may be applied to a color photographic product of the diffusion transfer type. In this case, processing in effected within the photographic material automatically. Suitable developing agents which are contained in a rupturable container include, in addition to Compounds (A) to (L), N-methylaminophenol, 1-phenyl-3-pyrazolidone, 1-phenyl-4,4-dimethyl-3-pyrazolidone, 1-phenyl-4-methylhydroxymethyl-3-pyrazolidone, 3-methoxy-N,N-diethyl-p-phenylenediamine, etc.

For the formation of color images in the photographic products used in the present invention, various methods can be employed which are based on the following principles: (i) the coupling reaction between a dye-forming color coupler and the oxidation product of a p-phenylenediamine type chromogenic developing agent, (ii) processing using a dye developer, (iii) an oxidative cleavage reaction of a DRR compound, (iv) the dye-releasing reaction caused by the coupling of a DDR coupler, (v) a dye-forming reaction caused by the coupling of a DDR coupler (vi) a silver dye bleach process and other conventionally known processes.

As is evident from the description heretofore, the method of the present invention can be applied to a wide variety of color photographic materials such as color positive film, color printing paper, color negative film, color reversal film, film units for color diffusion transfer, silver dye bleach photographic products, etc.

EXAMPLE 1

Into a mixture comprising 3 ml dibutyl phthalate and 5 ml ethyl acetate was dissolved 0.1 g of a dye having the following structure.

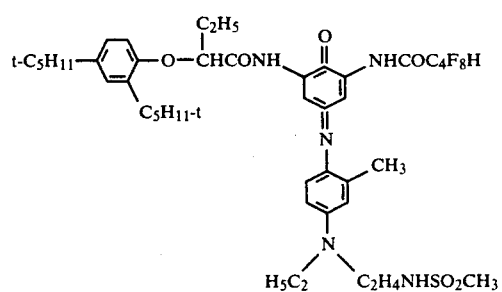

The resulting solution was emulsified in 10 g of a 10% aqueous gelatin solution containing 1 ml of a 1% sodium dodecylbenzenesulfonate aqueous solution.

The emulsified dispersion obtained above was further mixed with 10 g of a 10% gelatin solution and then spread over a substrate comprising a paper based laminated with polyethylene film on both surfaces thereof and dried to give Sample A.

Another sample (Sample B) was prepared in the same manner except that 50 mg of Compound I-2 characteristic of the present invention was further added to the emulsified dispersion described above. Further, Sample C was prepared similarly but with the addition of 100 mg of the following compound, a conventional fade preventing agent.

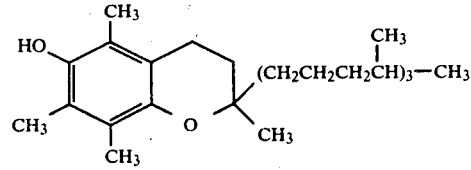

The coating conditions were adjusted so as to give a coating rate of the dye of 50 mg/m$^2$. The coating rate of the fade preventing agent in B and C was 30 mg/m$^2$.

In a Canon Tester (light intensity: 200,000 lux), a 48 hour fading test was performed on each of the samples superimposed with a UV cut filter C-40 (a product of the Fuji Photo Film Co.).

The results of the test are shown in Table 1 by the density values obtained by the measurement with a Macbeth Densitometer RD 514 loaded with a red filter of status AA grade.

TABLE 1

| Sample | Initial Density | Density after 48 Hour Fading | Remarks |
|---|---|---|---|
| A | 0.90 | 0.20 | Comparative sample |
| B | 0.92 | 0.50 | Invention |
| C | 0.88 | 0.25 | Comparative sample |

As the table demonstrates, Sample B containing the chelate complex of the present invention exhibits a superior light fastness. In this regard, it should be noted that in the past substantially no fade retarding agents have been known for cyan dyes.

EXAMPLE 2

0.1 g of the following compound was dissolved in a mixture comprising 3 ml tricresyl phosphate and 5 ml ethyl acetate.

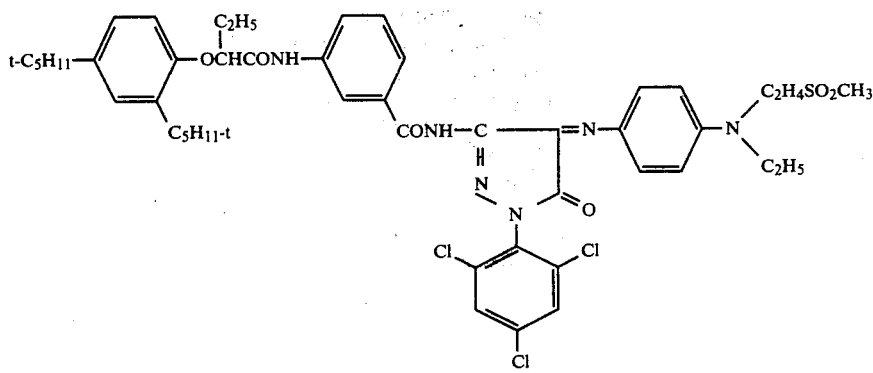

The resulting solution was dispersed in 10 g of a 10% gelatin solution containing 8 ml of a 1% sodium dodecylbenzenesulfonate aqueous solution. The resulting mixture was coated on a support comprising a paper base laminated on both sides with polyethylene film so as to give a coating rate of the dye of 60 mg/m² (Sample D) and dried.

A similar operation was repeated to provide Sample E with the addition of 50 mg of Compound I-3 characterizing the present invention. A Sample F was prepared by adding 200 mg of 2,5-di-tert-octylhydroquinone, as a conventional antioxidant. The same fading test was performed as in Example 1, giving the following results (See Table 2). The coating rate of Compound I-3 for Sample E was 30 mg/m² and the coating rate for Sample F of the conventional antioxidant was 120 mg/m².

TABLE 2

| Sample | Initial Density | Density after Fading Test | Remarks |
|---|---|---|---|
| D | 0.70 | 0.05 | Comparison |
| E | 0.70 | 0.40 | Invention |
| F | 0.72 | 0.15 | Comparison |

The density measurement was carried out with a Macbeth Reflective Densitometer RD 514 loaded with a green filter.

Table 2 clearly shows the superior performance obtained with Sample E.

EXAMPLE 3

10 g of a magenta coupler, 1-(2,4,6-trichlorophenyl)-3-(2-chloro-5-tetradecanamido)anilino-2-pyrazolino-5-one was dissolved in a mixture consisting of 10 ml tricresyl phosphate, 10 ml dimethylformamide and 15 ml ethyl acetate, and the resulting solution was emulsified in 80 g of a 10% gelatin solution containing sodium dodecylbenzenesulfonate. Then, the dispersion was blended into 145 g of a green sensitive silver chlorobromide photographic emulsion in which 7 g of silver was contained and in which the bromide content in the silver halide was 70 mol%. After the addition of a hardening agent and a coating aid, the mixture was spread over a support comprising a paper base laminated on both sides with polyethylene film to give Sample G. The coating rate of the coupler was 300 mg/m².

By repeating above procedures, Samples H and I were prepared wherein 0.5 g of Compound I-8 characterizing the present invention was added to the emulsified dispersion for Sample H and 2 g of 2,5-di-tert-butyl-hydroquinone was added for Sample I.

After exposure, each of these samples was processed with the following processing solutions.

| Developer | |
|---|---|
| Benzyl Alcohol | 15 ml |
| Diethylenetriaminepentaacetate | 5 g |
| KBr | 0.4 g |
| Na₂SO₃ | 5 g |
| Na₂CO₃ | 30 g |
| Hydroxylamine Hydrosulfate | 2 g |
| 4-Amino-3-methyl-N-ethyl-N-β-(methanesulfonamido)ethylaniline 3/2 H₂SO₄H₂O | 5 g |
| Water to make | 1,000 ml |
| | (pH = 10.1) |
| Blix Solution | |
| Ammonium Thiosulfate (70 wt %) | 150 ml |
| Na₂SO₃ | 5 g |
| Na[Fe(EDTA)] | 40 g |
| EDTA | 4 g |
| Water to make | 1,000 ml |
| | (pH = 6.8) |

| Processing Conditions | Temperature (°C.) | Time |
|---|---|---|
| Development | 33 | 3 min 30 sec |
| Blix | 33 | 1 min 30 sec |
| Rinse with Water | 28–35 | 3 min |

Each sample bearing a dye image was exposed to sunlight for 2 weeks through a UV cut filter C40 (a product of the Fuji Photo Film Co., which eliminates light with a wavelength shorter than 400 nm).

The results are summarized in Table 3. The degree of fading is expressed therein as the density drop in the area with the initial density of 2.0. The density was measured with a Macbeth Reflective Densitometer RD 514 (with a Status AA filter).

TABLE 3

| Sample | Density Drop by Fading Test | Remarks |
|---|---|---|
| G | 1.50 | Comparison |
| H | 0.40 | Invention |
| I | 1.00 | Comparison |

The table demonstrates the superior fade retarding effect of the complex compound of the present invention used in Sample H.

EXAMPLE 4

In 100 ml of dichloromethane were dissolved 50 mg of a dye having the following structure:

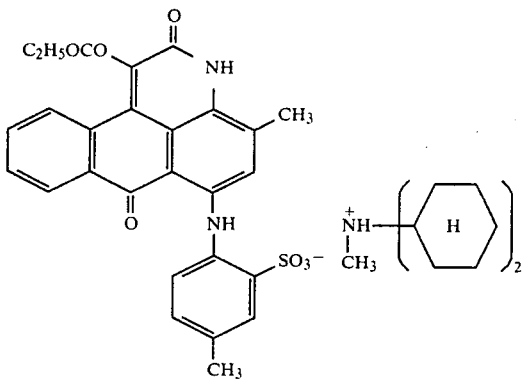

and 500 mg of polyester, Vylon 200 (manufactured by Toyo Spinning Co., Ltd.). The resulting solution was coated onto a glass plate using a spinner to prepare a film sample (Sample A). The film thickness was 5.5 μm. The coating rate of the dye was 500 mg/m².

In a similar manner, another film sample was prepared except that 5 mg of Compound I-2, coating rate 50 mg/m², of the present invention was further added in the solution (Sample B).

The film sample thus obtained were exposed to sunlight for one month and a color fading test was carried out. The results obtained are shown in Table 4, in which the density was measured at 550 nm.

TABLE 4

| Sample | Initial Density | Density after Color Fading Test |
|---|---|---|
| A | 1.0 | 0.40 |
| B | 1.0 | 0.80 |

The results clearly indicate that the chelate coupler of the present invention exhibits excellent light fastness in a dyed polyester.

Briefly summarizing the effects achieved by the metal chelate complex employed in the present invention:

(1) The metal chelate complex is readily soluble in organic solvents.

(2) In addition, the structure of the chelate complex can easily be modified so that it permits a large latitude for obtaining desired solubility.

(3) As a result of the latitude of its solubility, the complex is readily enveloped in oil droplets and, as a result, photographically undesired interaction with silver halide (e.g., desensitization) is avoidable.

(4) Due to its extremely light solubility, a small amount of the complex is sufficient to effect light fastness; conversely, a large amount can also be employed as in the case of umbrellas, agricultural vinyl cover sheets, etc.

(5) Where the chelate is used in a photographic element, no adverse effect on photographic properties is encountered.

(6) The complex is the first fading prevention agent suitable for improving the light fastness of cyan dye images.

For the reasons above, the metal chelate complex used in the present invention provides excellent light fastness.

While the invention has been described in detail and with reference to specific embodiments thereof, it will be apparent to one skilled in the art that various changes and modifications can be made therein without departing from the spirit and scope thereof.

What is claimed is:

1. A method of stabilizing a photographically useful organic substrate material selected from the group consisting of an anthraquinone, a quinoneimine, an azo, an azomethine, a methine, a polymethine, an indamine, an indophenol, a carbonium, an indigoid or a formazane dye and a fluorescent whitening agent against the action of light having an absorption peak between about 300 nm and about 800 nm in wavelength by making coexistant with said substrate material in an amount sufficient to stabilize said substrate material to light at least one compound represented by the following general formula (I):

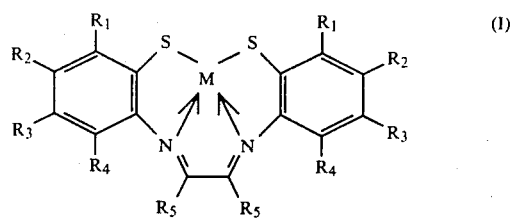

wherein M represents a metal atom selected from the group consisting of Cu, Co, Ni, Pd and Pt atoms; $R_1$, $R_2$, $R_3$ and $R_4$ may be the same or different and represent a hydrogen atom, a cyano group, a halogen atom, an alkyl group, an aryl group, a cycloalkyl group or a heterocyclic group which may be substituted or unsubstituted and which may be attached to the carbon atom in the benzene ring directly or through a divalent connecting group, or each of $R_1$ and $R_2$, $R_2$ and $R_3$, or $R_3$, and $R_4$ may combine to form the atomic group necessary to complete a 6-membered ring and $R_5$ represents a hydrogen atom or a methyl group.

2. The method of claim 1 which comprises incorporating into a medium containing said substrate material having an absorption peak between 300 and 800 nm a chelate compound represented by the general formula (I).

3. The method of claim 1, wherein said dye is formed from a dye forming coupler, a DDR coupler, a DRR coupler or a dye developer.

4. The method of claim 1, wherein said compound is represented by the following general formula (Ia):

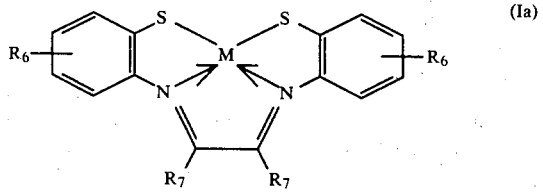

wherein M represents an atom selected from the group consisting of Cu, Co, Ni, Pd and Pt atoms; $R_6$ represents a hydrogen or halogen atom, a substituted or unsubstituted alkyl group, aryl group, cycloalkyl group or heterocyclic group which is attached to the carbon atom in the benzene ring directly or through a divalent connecting group and $R_7$ represents a hydrogen atom or a methyl group.

5. The method of claim 3, wherein said dye forming coupler is a yellow dye forming coupler, a magenta dye forming coupler or a cyan dye forming coupler.

6. The method of claim 4, wherein said coupler is a benzoylacetanilide or α-pivaloylacetanilide yellow dye forming coupler, a 5-pyrazolone, indazolone, pyrazolinebenzimidazole, pyrazole-s-triazole or cyanoacetylcoumarone magenta coupler or a phenol or naphthol cyan coupler.

7. A color photographic material comprising at least one layer containing a photographic dye image wherein said layer or an adjacent layer contains a compound of the formula (I) in an amount sufficient to stabilize said color photographic material to light:

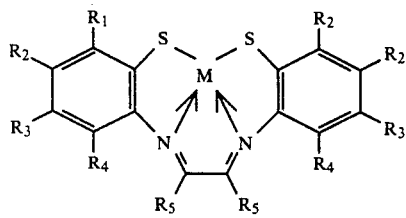

wherein M represents a metal atom selected from the group consisting of Cu, Co, Ni, Pd and Pt atoms; $R_1$ $R_2$, $R_3$ and $R_4$ may be the same or different and represent a hydrogen atom, a cyano group, a halogen atom, an alkyl group, an aryl group, a cycloalkyl group or a heterocyclic group which may be substituted or unsubstituted and which may be attached to the carbon atom in the benzene ring directly or through a divalent connecting group; or each of $R_1$ and $R_2$, and $R_3$, or $R_3$ and $R_4$ may combine to form the atomic group necessary to complete a 6-membered ring and $R_5$ represents a hydrogen atom or a methyl group.

8. The color photographic material of claim 7, wherein said photographic dye image is formed from a color coupler, a DDR coupler, a DRR compound, or a dye developer.

9. The photographic element of claim 7, wherein said dye is formed by the reaction of a primary aromatic amine color developing agent and a cyan, magenta, or yellow dye image forming coupler.

10. The photographic material of claim 7, wherein said compound is represented by the general formula (Ia):

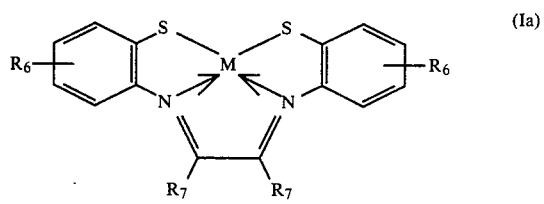

wherein M represents an atom selected from the group consisting of Cu, Co, Ni, Pd and Pt atoms; $R_6$ represents a hydrogen or halogen atom, a substituted or unsubstituted alkyl group, aryl group, cycloalkyl group or heterocyclic group which is attached to the carbon atom in the benzene ring directly or through a divalent connecting group and $R_7$ represents a hydrogen atom or a methyl group.

11. The photographic material of claim 7, wherein said dye is a methine, polymethine, indamine or indophenol dye.

12. The photographic material of claim 9, wherein said color coupler is a benzoylacetanilide or α-pivaloylacetanilide yellow dye forming coupler, a 5-pyrazolone, indazolone, pyrazolinebenzimidazole, pyrazole-s-triazole or cyanoacetylcoumarone magenta coupler or a phenol or naphthol cyan coupler.

* * * * *